(12) United States Patent
Elghanian et al.

(10) Patent No.: US 6,664,061 B2
(45) Date of Patent: *Dec. 16, 2003

(54) USE AND EVALUATION OF A [2+2] PHOTOADDITION IN IMMOBILIZATION OF OLIGONUCLEOTIDES ON A THREE-DIMENSIONAL HYDROGEL MATRIX

(75) Inventors: Robert Elghanian, Skokie, IL (US); Charles K. Brush, Whitefish Bay, WI (US); Yanzheng Xu, Buffalo Grove, IL (US)

(73) Assignee: Amersham Biosciences AB, Uppsala (SE)

( * ) Notice: Subject to any disclaimer, the term of this patent is extended or adjusted under 35 U.S.C. 154(b) by 24 days.

This patent is subject to a terminal disclaimer.

(21) Appl. No.: 09/928,250

(22) Filed: Aug. 9, 2001

(65) Prior Publication Data

US 2003/0124525 A1 Jul. 3, 2003

Related U.S. Application Data

(63) Continuation-in-part of application No. 09/344,620, filed on Jun. 25, 1999, now Pat. No. 6,372,813.
(60) Provisional application No. 60/232,305, filed on Sep. 12, 2000, and provisional application No. 60/224,070, filed on Aug. 9, 2000.

(51) Int. Cl.[7] .............................. C12Q 1/68; C08J 3/28
(52) U.S. Cl. .......................... 435/6; 522/114; 522/116; 522/117; 522/120
(58) Field of Search ................................ 522/114, 116, 522/117, 120; 435/6

(56) References Cited

U.S. PATENT DOCUMENTS

| | | |
|---|---|---|
| 3,826,678 A | 7/1974 | Hoffman et al. |
| 5,410,016 A | 4/1995 | Hubbell et al. |
| 5,563,056 A | 10/1996 | Swan et al. |
| 5,582,955 A | 12/1996 | Keana et al. |
| 5,595,741 A | 1/1997 | Huber et al. |
| 5,736,257 A | 4/1998 | Conrad et al. |
| 5,770,721 A | 6/1998 | Ershov et al. |
| 5,858,653 A | 1/1999 | Duran et al. |
| 5,905,024 A | 5/1999 | Mirzabekov et al. |
| 5,942,555 A | 8/1999 | Swanson et al. |
| 5,962,578 A | 10/1999 | Beihoffer et al. |
| 6,051,380 A | 4/2000 | Sosnowski et al. |
| 6,180,770 B1 | 1/2001 | Boles et al. |
| 6,372,813 B1 * | 4/2002 | Johnson et al. |

FOREIGN PATENT DOCUMENTS

| | | |
|---|---|---|
| DE | 39 19915 A1 | 6/1989 |
| EP | 0 226 470 | 6/1987 |
| EP | 0 386 644 | 9/1990 |
| WO | WO 90/15798 | 12/1990 |
| WO | WO 91/07087 | 5/1991 |
| WO | WO 97/27329 | 7/1997 |
| WO | WO 98/30575 | 7/1998 |
| WO | WO 00/31148 | 6/2000 |
| WO | WO 01/01143 | 1/2001 |
| WO | WO 01/84234 | 11/2001 |

OTHER PUBLICATIONS

An, et al. "Sequence–Specific Modification of Guanosine in DNA by a C60–Linked Deoxyoligonucleotide: Evidence for a Non–Singlet Oxygen Mechanism" Tetrahedron, vol. 52, No. 4, 1996 pp. 5179–5189.

Database WPI, "Immobilization of oligonucleotides on to a carrier by means of a covalent bond for production of oligonucleotide microarrays and chips" XP–002203841, AN 2000–423411, 2000.

Elsner, et al. "Use of Psoralens for Covalent Immobilization of Biomolecules in Solid Phase Assays" Bioconjugate Chemistry, 5, 1994, pp. 463–467.

Yousaf, et al. "Diels–Alder Reaction for the Selective Immobilization of Protein to Electroactive Self–Assembled Monolayers" J. Am. Chem. Soc., 121, 1999, pp. 4286–4287.

Burillo, S. G., "The Gamma–Ray–Induced Crosslinking of Polyacrylamide", Journal of Applied Polymer Sciences, vol. 32, No. 2, 1986, pp 3783–3789.

Hoyle, Charles et al., "Radiation Curing of Polymeric Materials", Acs Symposium Series, No. 417, copyright 1990, p. Nos. 2, 3, 4, 6, 8, 9, 10, 60, 67, 75 and 129.

Beena, Mathew et al., "Polymer–Metal Complexes of Amino Functionalized Divinylbenzne–Crosslinked Polyacrylamides", Database Compendex Accession Nos. EIX94071916060 and XP–002135596, Jun. 1993, p. 1.

Guschin, D., et al., Analytical Biochemistry, vol. 250, pp. 203–211 (1997).

Vasiliskov, A., et al., "Fabrication of Microarray of Gel–Immobilized Compounds on a Chip by Copolymerization," BioTechniques, vol. 27, pp. 592–606 (1999).

Cheng, J., et al., Nat. Biotechnol., vol. 16, pp. 541–546 (1998).

Finter, J., et al., Angew. Makromol. Chem., vol. 133, pp. 147–170 (1985).

Lockhart, et al., Nature Biotechnology, vol. 14, pp. 1675–1680 (1996).

Yamazaki, et al., J. Am. Chem. Soc., vol. 91, p. 520 (1969).

Weedon, A., Synthetic Organic Photochemistry, Chapter 2, W.M. Hoorspool (ed.) Plenum, New York, 1984.

Cargill, et al., J. Org. Chem., vol. 36, p. 1423 (1971).

Fan, J., et al., "Parallel Genotyping of Human SNPs Using Generic High–density Oligonucleotide Tag Arrays," Genome Research, vol. 10, Issue 6, pp. 853–860.

(List continued on next page.)

Primary Examiner—Ethan Whisenant
(74) Attorney, Agent, or Firm—Royal N. Ronning, Jr.

(57) ABSTRACT

[2+2] photo-attachable functional groups were incorporated in polyacrylamide based hydrogels and synthetic oligonucleotide probes. The probes were photochemically attached by covalent bonding to the three dimensional surface of a hydrogel.

94 Claims, 2 Drawing Sheets

OTHER PUBLICATIONS

Wodicka, L., et al., "Genome–wide expression monitoring in *Saccharomyces cerevisiae*," Nature Biotechnology, vol. 15, pp. 1359–1367 (1997).

Proudnikov, D., et al., "Immobilization of DNA in Polyacrylamide Gel for the Manufacture of DNA and DNA–Oligonucleotide Microchips," Analytical Biochemistry, vol. 259, pp. 34–41 (1998).

Alexa Fluor: Simply the Best and Brightest Fluorescent Conjugates, found at http://www.probes.com/media/publications/150.pdf.

Walker, M. A., "The Mitsunobu Reaction: A Novel Method for the Synthesis of Bifunctional Maleimide Linkers", Tetrahedron Letters, vol. 35, No. 5, 1994, pp 665–668.

Booker–Milburn, K. I. et al., "Stereoselective Intermolecular [2 +2] Photocycloaddition Reactions of Tetrahydrophthalic Anhydride and Derivatives with Alkenois and Alkynols", Tetrahedron Letters, vol. 55, 1999, pp 5875–5887.

Saarela, J., "Candidate Regions in MS Monitored Using SNP Microarray", Federation of American Societies for Experimental Biology: *Quality Life Through Research*, webpage http://www.faseb.org/genetics/ashg99/f2513.htm, Jul. 28, 2001.

Cronin, F., "Applying Rapid DNA Microarray Optimization Capability to SNP Screening and Genotyping", Federation of American Societies for Experimental Biology: *Quality Life Through Research*, webpage http://www.faseb.org/genetics/ashg99/f1238.htm, Jul. 28, 2001.

Junnarkar, Sandeep, "GeneChip' Encodes DNA on Silicon", *The New York Times* on the web, webpage http://nytimes.com/library/cyber/week/031597genechip.html, Jul. 28, 2001.

Agilent Technologies, Agilent Technologies to expand presence in life science market with its first human cDNA microarray, webpage http://.agilent.com/about/newsroom/presrel/2001/16may2001a.html, Jul. 28, 2001.

Vasiliskov, A., et al., "Fabrication of Microarray of Gel–Immobilized Compounds on a Chip by Copolymerization," BioTechniques, vol. 27, pp. 592–606 (1999).

Rehman, et al., "Immobilization of acrylamide–modified oligonucleotides by co–polymerization," Nucleic Acids Research, vol. 27, No. 2, pp. 649–655 (1999).

Fan, J., et al., "Parallel Genotyping of Human SNPs Using Generic High–density Oligonucleotide Tag Arrays," Genome Research, vol. 10, Issue 6, pp. 853–860, (2000).

Wodicka, L., et al., "Genome–wide expression monitoring in *Saccharomyces cerevisiae*," Nature Biotechnology, vol. 15, pp. 1359–1367 (1997).

Proudnikov, D., et al., "Immobilization of DNA in Polyacrylamide Gel for the Manufacture of DNA and DNA–Oligonucleotide Microchips," Analytical Biochemistry, vol. 259, pp. 34–41 (1998).

Pieles, U., et al., "Psoralen covalently linked to oligodeoxyribonucleotides: synthesis, sequence specific recognition of DNA and photo–cross–linking to pyrimidine residues of DNA," Nucleic Acids Research, vol. 17, No. 1, pp. 285–299 (1989).

* cited by examiner

FIGURE 1

| KEY: | |
|---|---|
| C.A. | Methacrylamide |
| T.A. | Thymine/Methacrylamide |
| CINN | Cinnamide |
| L | Linker |

FIGURE 2

USE AND EVALUATION OF A [2+2] PHOTOADDITION IN IMMOBILIZATION OF OLIGONUCLEOTIDES ON A THREE-DIMENSIONAL HYDROGEL MATRIX

REFERENCE TO RELATED APPLICATIONS

This application is a continuation-in-part of U.S. Nonprovisional Application No. 09/344,620, filed Jun. 25, 1999, now U.S. Pat. No. 6,372,813, entitled "Methods and Compositions for Attachment of Biomolecules to Solid Supports, Hydrogels, and Hydrogel Arrays", and claims the benefit of U.S. Provisional Application No. 60/224,070, filed Aug. 9, 2000, entitled "Use and Evaluation of 2+2 Photoaddition in Immobilization of Oligonucleotides on A Three Dimensional Hydrogel Matrix", which is incorporated by reference, and U.S. Provisional Application No. 60/232,305, filed Sep. 12, 2000, entitled "The Use and Evaluation of 2+2 Photoaddition in Immobilization of Oligonucleotides on A Three Dimensional Hydrogel Matrix", which is incorporated by reference.

BACKGROUND

Chip based DNA microarrays are an integration of circuit fabrication technology and genetics. DNA microarrays consist of matrices of DNA arranged on a solid surface where the DNA at each position recognizes the expression of a different target sequence. Microarrays are used to identify which genes are turned on or off in a cell or tissue, and to evaluate the activity level under various conditions. This knowledge enables researchers to determine whether a cell is diseased or the effect of a drug on a cell or group of cells. These studies are critical to determine a drug's efficacy or toxicity, to identify new drug targets, and to more accurately diagnose illnesses, such as specific types of cancer. The technology is useful to classify tumors with the hope of establishing a correlation between a specific type of cancer, the therapeutic regiment used for treatment, and survival.

Photolithography technology, similar to that employed for transistor etching into silicon chips, is often used to layer chains of nucleotides, the basic units of DNA, onto silicon. Additionally, nucleotides, often referred to as "probes," may be deposited onto solid substrates, or solid substrates coated with various polymers. Various deposition or spraying methods are used to deposit the nucleotides, including piezoelectric technology similar to that used for ink-jet printer heads and robotic methods. The probes are attached to the substrates or polymers by thermal, chemical, or light-based methods to form the microarray.

The genes of interest, or "targets," are generally put into solution in a "fluidics station" which disperses the target solution on the microarray surface. If fluorescence detection is to be used, the targets may be tagged with fluorescent labels. Nucleotide targets which are complementing, or "recognized" by, the nucleotide probes on the support or polymer then bind, or hybridize, with their corresponding probes. Additionally, the targets may be enzymatically tagged after hybridization to their respective probes. After rinsing to remove any unbound targets from the microarray, the presence and or concentration of specific targets is determined by spectroscopic or other methods.

Many beneficial applications exist for microarrays, including diagnosing mutations in HIV-1, studying the gene defects which lead to cancer, polymorphism screening and genotyping, and isolating the genes which lead to genetic based disorders, such as multiple sclerosis.

A microarray is generally formed by coating a solid support with a polymer. Acrylamide ($CH_2=CHC(O)NH_2$; C.A.S. 79-06-1; also known as acrylamide monomer, acrylic amide, propenamide, and 2-propenamide) is an odorless, free-flowing white crystalline substance that is used as a chemical intermediate in the production and synthesis of polyacrylamide polymers. Polyacrylamides have a variety of uses and can be modified to optimize nonionic, anionic, or cationic properties for specified uses, such as a polymer coating for the solid support of a microarray.

Polyacrylamide hydrogels are often used as molecular sieves for the separation of nucleic acids, proteins, and other moieties, and as binding layers to adhere to the surfaces biological molecules including, but not limited to, proteins, peptides, oligonucleotides, polynucleotides, and larger nucleic acid fragments. The gels currently are produced as thin sheets or slabs, typically by depositing a solution of acrylamide monomer, a crosslinker such methylene bisacrylamide, and an initiator such as N, N, N', N'-tetramethylethylendiamine (TEMED) between two glass surfaces, such as microscope slides. A spacer is used to obtain the desired thickness of polyacrylamide.

Generally, the acrylamide polymerization solution is a 4–5% solution (acrylamide/bisacrylamide 19/1) in water/glycerol, with a nominal amount of initiator added. The solution is polymerized and crosslinked either by ultraviolet (UV) radiation (e.g., 254 nm for at least about 15 minutes, or other appropriate UV conditions, collectively termed "photopolymerization"), or by thermal initiation at elevated temperature, typically about 40° C. Following polymerization and crosslinking, the top glass slide is removed from the surface to uncover the gel. The pore size (or "sieving properties") of the gel is controlled by changing the amount of crosslinker and the % solids in the monomer solution. The pore size also can be controlled by changing the polymerization temperature.

In the fabrication of polyacrylamide hydrogel arrays used as binding layers for biological molecules, the acrylamide solution typically is imaged through a mask during the UV polymerization/crosslinking step. The top glass slide is removed after polymerization, and the unpolymerized monomer is washed away with water leaving a fine feature pattern of polyacrylamide hydrogel, the crosslinked polyacrylamide hydrogel pads.

Further, in an application of lithographic techniques known in the semiconductor industry, light can be applied to discrete locations on the surface of a polyacrylamide hydrogel to activate these specified regions for the attachment of an anti-ligand, such as an antibody or antigen, hormone or hormone receptor, oligonucleotide, or polysaccharide, to the hydrogel (PCT International Application WO 91/07087, incorporated by reference). Following fabrication of the hydrogel array, the polyacrylamide subsequently is modified to include functional groups for the attachment of probes. The probes, such as DNA, are later attached.

Chemical immobilization of biomolecules, such as DNA, RNA, peptides, and proteins, on a solid support or within a matrix material, such as a hydrogel, has become a very important aspect of molecular biology research. This is especially true in the manufacturing and application of microarray or chip-based technologies where biomolecules are immobilized as probes.

Typical procedures for attaching a biomolecule to a surface involve multiple reaction steps, often requiring chemical modification of the hydrogel to provide the chemical functionality for covalent bonding with the biomolecule. The efficiency of the attachment chemistry and strength of the chemical bonds formed are critical to the fabrication and ultimate performance of the microarray.

For polyacrylamide, the necessary functionality for probe attachment presently entails chemical modification of the hydrogel through the formation of amide, ester, or disulfide bonds after polymerization and crosslinking of the hydrogel. An unresolved problem with this approach is the less than optimal stability of the attachment chemistry over time, especially during subsequent manufacturing steps, and under use conditions where the microarray is exposed to high temperatures, ionic solutions, and multiple wash steps. Such conditions promote continued depletion in the quantity of probe molecules present in the array, thus reducing its performance and useful life. A further problem is the low efficiency of the method.

Another approach that has been employed is the polymerization of a suitable "attachment co-monomer" into the polyacrylamide matrix that is capable of bonding with the DNA oligonucleotide probe. However, this method is limited in that the incorporation of the attachment co-monomer as a third component of the matrix, along with the acrylamide monomer and crosslinker, can give rise to problems during acrylamide polymerization. These problems include an inability to form the matrix, a loss of mechanical integrity in the matrix, and a loss of adhesion between the matrix and the solid support.

A more recent method has employed direct co-polymerization of an acrylamide-derivatized oligonucleotide. For instance, ACRYDITE (Mosaic Technologies, Boston, Mass.) is an acrylamide phosphoramidite that contains an ethylene group capable of free radical polymerization with acrylamide. Acrydite-modified oligonucleotides are mixed with acrylamide solutions and polymerized directly into the gel matrix (Rehman et al., Nucleic Acids Research, 27, 649–655 (1999). This method still relies on acrylamide as the monomer. Depending on the choice of chemical functionality, similar problems in the stability of attachment, as with the above-mentioned methods, also result.

Accordingly, the prior art methods use post-modification of the matrix, or incorporation of a suitable co-monomer during the fabrication process. In addition to the disadvantages described above, toxic acrylamide monomer is used in manufacturing the arrays.

The present invention seeks to overcome some of the aforesaid disadvantages of the prior art, including the problems associated with chemical attachment of the probes to the polymer-coated support, for the purpose of forming microarrays useful in expression and single nucleotide polymorphism (SNP) analysis. In particular, the present invention provides methods of performing expression and SNP microarray analysis to determine the presence and/or concentration of a target, wherein a microarray is formed by attaching a polymer-coated support and a probe by a [2+2] cycloaddition reaction, wherein the reaction is between reactive sites on the polymer and probe. These and other objects and advantages of the present invention, as well as additional inventive features, will be apparent from the description of the invention provided herein.

BRIEF SUMMARY

Novel hydrogel arrays are used to detect specific target oligonucleotides, including mRNA and DNA. Expression and single nucleotide polymorphism analyses are performed. The arrays are constructed from polyacrylamide based hydrogels and synthetic oligonucleotide probes that are functionalized with reactive groups. The reactive groups undergo [2+2] type photocycloaddition when exposed to ultraviolet light. This cycloaddition results in the probes being covalently attached to the hydrogel.

DETAILED DESCRIPTION

The current invention relates to a novel method of performing gene analyses, including expression and SNP, using hydrogel microarrays in which acrylamide is polymerized in a controlled fashion to obtain a "prepolymer", which is then photochemically crosslinked and attached using [2+2] photocycloaddition chemistry to oligonucleotide probes, including DNA. For the [2+2] photocycloaddition to occur, the prepolymer and probes contain reactive sites, which are inherent or added by chemical means, that form covalent bonds upon irradiation with light.

Generally, microarrays are a collection of probe binding sites at known physical locations bound on a surface. By positioning tiny specks of probe molecules at known surface locations and then exposing a collection of target molecules to the probes, selective binding occurs between specific probes and targets. For example, because adenine only binds to thymine, a thymine probe will selectively bind to an adenine target.

Once probe/target binding occurs, unbound targets are washed away and the microarray is analyzed to determine which targets have bound at what probe locations on the microarray. If an internal standard is included with the targets, and probes are provided for the standard on the microarray, quantitative determinations may also be made. Because a plethora of different probes can be deposited on a single microarray, numerous types of binding analyses can be simultaneously performed.

Expression/Targets

Expression microarrays are used to detect the presence of nucleic acids or polynucleotides generated, or expressed, by genes. These nucleic acids, or "targets," are preferably messenger RNA, RNA, DNA, amplified RNA, amplified DNA or modifications thereof, and more preferably mRNA, DNA, or RNA. They may be taken from any biological source, including healthy or diseased tissue, tissues that have been exposed to drugs, and pathogens. Because expression microarrays are often used to determine if a tissue is expressing different biomolecules than normal due to disease or drug treatment, the targets of interest are often nucleotides produced by these tissues.

Labels

In an expression microarray, the targets of interest are labeled with dyes or other compounds that fluoresce when irradiated with light of a known wavelength. The labels are attached to the targets by standard chemical/enzymatic methods known to one of skill in the art, as found in Lockhart, et al., *Nature Biotechnology*, 14: 1675–80, (1996), for example. The fluorescent emission from the labeled nucleic acids allows their detection by spectroscopic methods. By scanning the expression microarray with light at the excitation wavelength or wavelengths of the dyes used, the labeled nucleic acids may be detected. By placing different dyes on different targets, multiple determinations may be made from a single microarray.

The literature contains examples of many fluorescent dyes suitable for labeling the targets. Preferred labels include those sold under the tradename ALEXA FLUOR. These labels are dyes with trade secret compositions which may be purchased from Molecular Probes, Inc. (849 Pitchford Avenue, Eugene, Oreg. 97402-9165 USA). Other preferred labels include the cyanine dyes prepared with succinimidyl ester reactive groups, such as Cy-3, Cy-5, Cy-5.5. The number immediately after the "Cy" indicates the number of bridge carbons. The number following the decimal point indicated a unique dye structure, which is determined by the substituents on the structure. Cy-3, Cy-5, and Cy-5.5 are available from Amersham Pharmacia Biotech (Piscataway, N.J., USA). Cy-3 is most preferred.

Standards

In addition to determining the presence of a specific nucleic acid, expression microarrays may be used to simultaneously make a quantitative determination of the detected targets. This is possible by incorporating "probe standards" into the microarray which selectively bind to specific "target standards," but do not interfere with analyte probe/target binding. Preferred target standards are yeast mRNA and bacterial mRNA, or combinations thereof. Yeast mRNA is most preferred.

Like the target being analyzed, the target standards are also fluorescently labeled to allow detection and quantitation. When scanned, the fluorescence intensity of the labeled targets is compared with that of the labeled target standards to determine the ratio of target to target standard. By combining a known amount of target standard with the sample containing the target, a quantitative target determination is made. Preferably, probe and probe standards are applied to the hydrogel in about equal amounts.

An expression microarray is performed by first preparing an aqueous target solution containing the targets of interest in an aqueous buffer solution. Preferably, the target solution contains a buffer suitable to maintain pH from about 6 to 9, more preferably the solution contains a phosphate and sodium chloride buffer, most preferably the solution contains about 700 mmol. of sodium chloride and 100 mmol. of a phosphate. Useful buffers may be made from purchased reagents or bought pre-prepared from SIGMA (St. Louis, Mo.), among others. If a quantitative determination is desired, a known concentration of target standards is also added to the aqueous target solution.

After dispersing the aqueous target solution on the microarray, the microarray is developed. Development is preferably conducted for the minimum amount of time required to obtain useful results. This time may range from minutes to hours, depending on conditions and may be performed in an enclosed miniaturized chamber. Preferably, development continues for 1 minute to 42 hours, more preferably for 10 minutes to 24 hours and most preferably for about 16 hours. Development is preferably conducted from 25 to 50° C., more preferably from 30 to 45° C., and most preferably at about 37° C.

After development is completed, the microarray is cooled to about room temperature and washed with an appropriate aqueous wash solution to remove unbound targets. Preferably, the solution contains a phosphate buffer, more preferably the solution contains a phosphate and sodium chloride buffer, most preferably the solution contains about 300 mmol. of sodium chloride and 100 mmol. of a phosphate. Useful buffers may be made from purchased reagents or bought pre-prepared from SIGMA (St. Louis, Mo.), among others. Although not required, a buffer similar to that used for the aqueous target solution may be used, albeit with a lower sodium chloride concentration.

After drying at about room temperature, the microarray is scanned in an appropriate spectrophotometer to collect fluorescence position and optionally, intensity data. If Cy-3 is used as the fluorescent label for the targets, scanning is conducted at 532 nanometers. Other scanning wavelengths are possible, as dictated by the labels used. A preferable scanner is an AXON SERIES A, available from AXON INSTRUMENTS, Union City, Calif., or equivalent. For quantitative analysis, the scanner, or optional processor, computes the intensity ratio of target to target standard fluorescence.

SNP

Generally, single nucleotide polymorphism (SNP) microarrays are similar to expression microarrays, including their use of oligonucleotide probes and nucleic acid targets. However, significant differences exist regarding how fluorescent labels are attached to the targets and how the microarrays are developed. For an expression microarray, the targets are labeled prior to their dispersion on the microarray. Conversely, for an SNP array, the aqueous target solution, in addition to buffers, contains non-labeled targets, an active enzyme, a fluorescently labeled carrier, and optionally, target standards.

While expression microarrays rely on selective probe/target binding to generate a fluorescent pattern on the array, SNP microarrays rely on enzyme selective single base extension (SBE) of a selected probe/target complex. During development of the SNP microarray, the targets bind to their respective probes to form a complex, generally having a double-helix structure. If an appropriate complex is recognized by the active enzyme, it transfers the label by a SBE reaction from the carrier to the complex. Thus, fluorescent probe/target sites are selectively created. The SNP microarray may then be washed and scanned similarly to an expression array to confirm the presence of a specific target, and optional quantitation, if probe and target standards are used.

Preferable active enzymes include any enzyme capable of transferring a label to a probe/target complex by SBE. More preferable enzymes include labeled thermosequanase and other DNA polymerases, or combinations thereof. Most preferred is thermosequanase, available from Amersham Pharmacia Biotech (Piscataway, N.J., USA). Preferable fluorescent label carriers include any carrier which can provide a transferable label to an active enzyme for transfer to a probe/target complex. More preferable fluorescent label carriers include labeled dideoxynucleotide triphosphate and other labeled synthetic di-deoxy cyclic or acyclic nucleotides, or combinations thereof. Most preferred is labeled dideoxynucleotide triphosphate.

Another difference between expression microarrays and SNP microarrays is the development and washing processes. SNP development entails cycling the temperature preferably between 20 and 80° C., more preferably between 30 and 70° C., and most preferably between 40 and 60° C. for preferably 20 to 70 heating/cooling cycles, more preferably for 30 to 60 heating/cooling cycles, and most preferably for 40 to 50 heating/cooling cycles. The wash is also conducted with a similar wash solution as used to wash an expression microarray, but the aqueous solution is preferably between 30 and 80° C., more preferably between 40 and 70° C., and most preferably between 50 and 60° C.

Solid Support

Generally, the polymer or polyacrylamide reactive prepolymer is coated onto a solid support. Preferably, the "solid support" is any solid support that can serve as a support for the polyacrylamide prepolymer, including film, glass, silica, modified silicon, ceramic, plastic, or polymers such as (poly)tetrafluoroethylene, or (poly)vinylidenedifluoride. More preferably the solid support is a material selected from the group consisting of nylon, polystyrene, glass, latex, polypropylene, and activated cellulose. Most preferably, the solid support is glass.

The solid support can be any shape or size, and can exist as a separate entity or as an integral part of any apparatus, such as beads, cuvettes, plates, and vessels. If required, the support may be treated to provide adherence of polyacrylamide to the glass, such as with γ-methacryl-oxypropyl-trimethoxysilane ("Bind Silane," Pharmacia). In particular, covalent linkage of polyacrylamide hydrogel to the solid support can be done as described in European Patent Application 0 226 470, incorporated by reference. The solid support may optionally contain electronic circuitry used in the detection of bit molecules, or microfluidics used in the transport of micromolecules.

Polymer

Preferably, the solid support is coated with an acrylamide prepolymer, which may be coated and imaged using standard commercial equipment. The prepolymer is non-toxic, easily handled, can be manufactured in highly consistent batches, and has good viscosity characteristics for coating surfaces during microarray manufacture. The synthesis and use of prepolymers for gel pad formation is described, for example, in U.S. application Ser. No. 60/109,821, filed Nov. 25, 1998.

Although further modification, including crosslinking and/or probe attachment, of the prepolymer is not required after synthesis, the prepolymer can be functionalized by the addition of one or more reactive sites. A detailed description of polyacrylamide hydrogels and hydrogel arrays made from polyacrylamide reactive prepolymers is given in U.S. patent application Ser. No. 09/344,217, filed Jun. 25, 1999, entitled "Polyacrylamide Hydrogels and Hydrogel Arrays Made from Polyacrylamide Reactive Prepolymers", incorporated by reference in its entirety.

Conversion of the prepolymer into a three-dimensional polyacrylamide hydrogel array, as preferred for the current invention, may entail additional steps, including developing the pattern in the array and removing any uncrosslinked polymer. Pattern development can be accomplished by exposing the reactive prepolymer through a photomask. Uncrosslinked polymer may also be removed by aqueous solution.

Preferably, the polymer is a polymer or copolymer made of at least two co-monomers that form a three-dimensional hydrogel, wherein at least one of the co-monomers can react by [2+2] photocycloaddition. Alternatively, the polymer is a polymer or copolymer that forms a three-dimensional hydrogel which is then chemically modified to contain a reactive site that undergoes [2+2] photocycloaddition.

Most preferably, the polymer is an acrylamide reactive prepolymer made by polymerizing acrylamide with a compound including dimethyl maleimide (DMI), a six carbon linker, and a polymerizable group, such as acrylate, to give a low molecular weight polymer. While not wishing to be bound by any particular theory, it is thought that when the reactive prepolymer is later crosslinked to form a three-dimensional hydrogel, the polymerizable group attaches to the acrylamide to form the hydrogel and the dimethyl maleimide attaches the resultant hydrogel to the solid support, and optionally to the probe if crosslinking and probe attachment are performed concurrently. During this process, it is believed that about 50% of the [2+2] photoreactive sites on the DMI remain available for probe attachment.

Probes

Probes are attached to the polymer by [2+2] photocycloaddition between reactive sites on the polymer or reactive prepolymer and the probe. Preferable probes are nucleic acids or fragments thereof containing less than about 5000 nucleotides, especially less than about 1000 nucleotides. Most preferably, a probe is an oligonucleotide, such as DNA or modifications thereof. Probes may be tissue or pathogen specific Preferably, probes or biomolecules inherently contain reactive sites or have been functionalized with a reactive site by chemical means. Preferred probes requiring no further modification include certain nucleic acid species that incorporate pyrimidines such as thymine. Other preferred probes are modified to contain thymine or polythymine, or proteins incorporating thiols. A detailed description of suitable probes, reactive sites, and applicable probe modifications to allow [2+2] cycloadditions is given in U.S. patent application Ser. No. 09/344,620, filed Jun. 25, 1999, entitled "Method and Compositions for Attachment of Biomolecules to Solid Supports, Hydrogels and Hydrogel Arrays", incorporated by reference in its entirety.

Reactive Sites

Modified DNA oligonucleotides or polynucleotides are employed as probes that include a reactive site capable of undergoing [2+2] photocycloaddition. Additionally, the hydrogel polymer supports include reactive sites that are capable of undergoing [2+2] photocycloaddition. When irradiated with ultraviolet light at an appropriate wavelength, the probes are then attached to the hydrogel by [2+2] cycloaddition between the reactive sites. Typically the reactive site is introduced into the nucleic acid species by synthesizing or purchasing DNA functionalized with amine which is then reacted with the molecule having the desired reactive site to obtain DNA having the reactive site. Maleimide or acrylate functionalized DNA are examples.

Preferable reactive sites include, dimethyl maleimide, maleimide, acrylate, acrylamide, vinyl, cinnamyl groups from cinnamic acid, cinnamate, chalcones, coumarin, citraconimide, electron deficient alkenes such as cyano alkene, nitro alkene, sulfonyl alkene, carbonyl alkene, arylnitro alkene, pyrimidine bases, thymine, and polythymine. Most preferred are acrylate, thymine, and dimethyl maleimide (DMI).

Reactive sites may be attached to the probe either directly or with an appropriate intermediate. A preferred intermediate is phosphoramidite. Most preferably, phosphoramidite is functionalized with a cinnamide and then attached to the oligonucleotide (5' position for DNA) to form a probe ready for [2+2] photocycloaddition. Other preferred reactive sites are as described in Guillet, "Polymer Photophysics and Photochemistry", Chapter 12 (Cambridge University Press: Cambridge, London).

Additionally, molecules having a structure similar to dimethyl maleimide may be employed as reactive sites on the probes, including maleimide/N-hydroxysuccinimide (NHS) ester derivatives. Such preferred maleimide/NHS esters include 3-maleimidoproprionic acid hydroxysuccinimide ester; 3-maleimidobenzoic acid N-hydroxy succinimide; N-succinimidyl 4-malimidobutyrate; N-succinimidyl 6-maleimidocaproate; N-succinimidyl 8-maleimidocaprylate; N-succinimidyl 11-maleimidoundecaoate. These esters can be obtained from a variety of commercial vendors, such as ALDRICH (Milwaukee, Wis.).

Reactive sites can yield homologous linking, where a probe reactive site cyclizes with a hydrogel reactive site having the same chemical structure, or for heterologous linking, where a probe reactive site cyclizes with a hydrogel reactive site having a different chemical structure. Preferred homologous linking occurs between DMI reactive sites on the probe and hydrogel, while preferred heterologous linking occurs between acrylate reactive sites on the probe and DMI reactive sites on the hydrogel. cDNA is a preferred probe for either type of cyclization.

Linkers

Reactive sites can be attached to probes through linkers. An example is the attachment of maleimide to a synthetic oligonucleotide bearing a primary amine at the 5' end. 3-Maleimidopropionic acid hydroxysuccinimide ester reacts with the primary amine to yield an oligonucleotide bearing the maleimide group, which can then be coupled to dimethyl maleimide in a hydrogel by a [2+2] photocycloaddition. A similar reaction can be done on the free E-amino group of lysine in a protein to provide a maleimide group for 2+2 coupling of the protein to the hydrogel. Other attachment methods are described in Hermanson, *Bioconjugation Chemistry*.

Preferably, probes include a linker region. The linker region is a portion of the molecule which physically separates the reactive site, which undergoes [2+2] photocycloaddition, from the remainder of the molecule. A linker region may also separate a reactive site from the polymer support. Although not wishing to be bound by any particular theory, it is thought that the linker region separates the portion of the probe, which is recognized by the target, thus making the probe more "available" for recognition by the target or enzyme.

Such linker regions are known and have been described in the art, and in some cases, may be commercially available, such as biotin (long arm) maleimide, available from GLEN RESEARCH, Sterling, Va., for example. Any linker region can be employed, so long as the linker region does not negate the desirable properties of the biomolecule, including the ability of the nucleic acid species to function as a probe. Preferred linker regions are organic chains of about 6 to 100 atoms long, such as $(CH_2)_6 NH$, $(CH_2CH_2O)_5CH_2CH_2NH$, etc. Additionally, linkers may be linked to each other, or to different types of linkers, to extend their chain length.

[2+2] Photocycloaddition

According to the invention, "cyclization" or "photocycloaddition" is a light-induced reaction between two reactive groups, at least one of which is electronically excited. Advantageously, photocyclization reactions can be made to proceed with high efficiency. Photocycloaddition includes cyclodimerization and preferably includes [2+2] photocycloaddition. Preferably, photocycloaddition is of the "[2+2]" variety, wherein two carbon-carbon or carbon-heteroatom single bonds are formed in a single step. The [2+2] cycloaddition involves addition of a $2\pi$-component of a double bond to the $2\pi$-component of a second double bond. Alternatively, the reaction may proceed by way of a $2\pi$-component of triple bonds. Under the rules of orbital symmetry, such additions are thermally forbidden, but photochemically allowed. Such reactions typically proceed with a high degree of stereospecificity and regiospecificity.

Photochemical [2+2] cycloaddition of the probe to the hydrogel is obtained as follows. A reactive site is incorporated into the probe. A second reactive site is incorporated into the polyacrylamide hydrogel following or as part of its polymerization, and prior to crosslinking. The combination is then irradiated with light at the appropriate wavelength to induce [2+2] photocycloaddition, which results in the probe being bound to the hydrogel. Optionally, a photosensitiser may be added to the hydrogel or reactive prepolymer to increase the efficiency of the photocycloaddition reaction. Preferred photosensitisers include water soluble quinones and xanthones, including anthroquinone, sulfonic acid quinone, benzoin ethers, acetophenones, benzoyl oximes, acylphosphines, benzophenones, and TEMED (N,N,N',N'-tetramethylethylendiamine). Anthroquinone-2-sulfonic acid is most preferred and is available from ALDRICH, Milwaukee, Wis.

Preferred [2+2] cycloadditions include those between two carbon-carbon double bonds to form cyclobutanes and those between alkenes and carbonyl groups to form oxetanes. Photocycloadditions between 2 alkenes to form cyclobutanes can be carried out by photo-sensitization with mercury or directly with short wavelength light, as described in Yamazaki et al., *J. Am. Chem. Soc.*, 91, 520 (1969). The reaction works particularly well with electron-deficient double bonds because electron-poor olefins are less likely to undergo undesirable side reactions. Photocycloadditions between carbon-carbon and carbon-oxygen double bonds, such as $\alpha,\beta$-unsaturated ketones, form oxetanes (Weeden, *In Synthetic Organic Photochemistry*, Chapter 2, W. M. Hoorspool (ed.) Plenum, N.Y., 1984) and enone addition to alkynes (Cargill et al., *J. Org. Chem.*, 36, 1423 (1971)).

Microarray Formation

Hydrogel microarrays are formed by applying the polyacrylamide reactive prepolymer to a solid support and then attaching the desired probes by [2+2] photocycloaddition to give a three-dimensional hydrogel with probes embedded in an array pattern. The reactive prepolymer is also crosslinked to form a hydrogel. Preferably, crosslinking occurs either prior to or simultaneously with probe attachment. Crosslinking of the prepolymer and probe attachment is preferably done with ultraviolet irradiation. Prior to irradiation with ultraviolet light to photocyclize the reactive sites on the probes with those on the reactive prepolymer or hydrogel, the probes are dispersed at known array locations on the reactive prepolymer or crosslinked hydrogel. Piezoelectric or other methods may be used to disperse the solution containing the probes and optional probe standards.

EXAMPLES

Example 1

This example demonstrates the sensitivity of a microarray of the present invention. Three probes on the microarray represent each gene. For photochemical attachment experiments, probes directed against eight different yeast mRNAs were included on the chip to determine sensitivity. One $\mu$g of human placental poly(A)$^+$ RNA was spiked with 17 pg of yeast poly(A)$^+$ RNA in an aqueous buffer solution containing 700 mmol. NaCl and 100 mmol. phosphate to form an aqueous target solution. The aqueous solution was the added to the array and incubated at 37° C. for about 16 hours. The microarray was then washed with an aqueous buffer containing 300 mmol. NaCl and 100 mmol. phosphate to remove any unbound RNA and allowed to dry. The developed and washed microarray was then transferred to an Axon Series A scanner.

Figure 1:
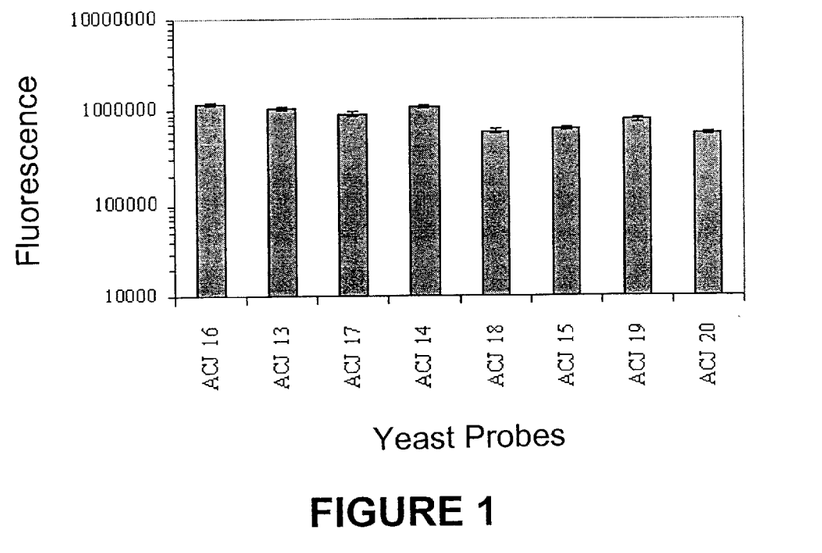
FIG. 1 shows a plot of the fluorescence intensities of different yeast transcripts detected on an expression microarray when each was spiked into human placental poly (A)+ mRNA at a mass ratio of 1 in 300,000 (about one copy per cell).

FIG. 1 shows a plot of the fluorescence intensity of different yeast transcripts detected when each was spiked into human placental poly (A)+ RNA at a mass ratio of 1 in 300,000 (equivalent to about one copy per cell). Seven out of eight probes (each probe corresponding to a different yeast transcript) were significantly over the background cutoff fluorescence signal. Cutoff is defined as the mean signal of the blank pads plus three standard deviations which gives a 99.7% likelihood of having a real signal. The sensitivity of the assay on this platform has thus been shown to be down to 17 pg of starting poly (A)+ RNA.

Example 2

Figure 2:
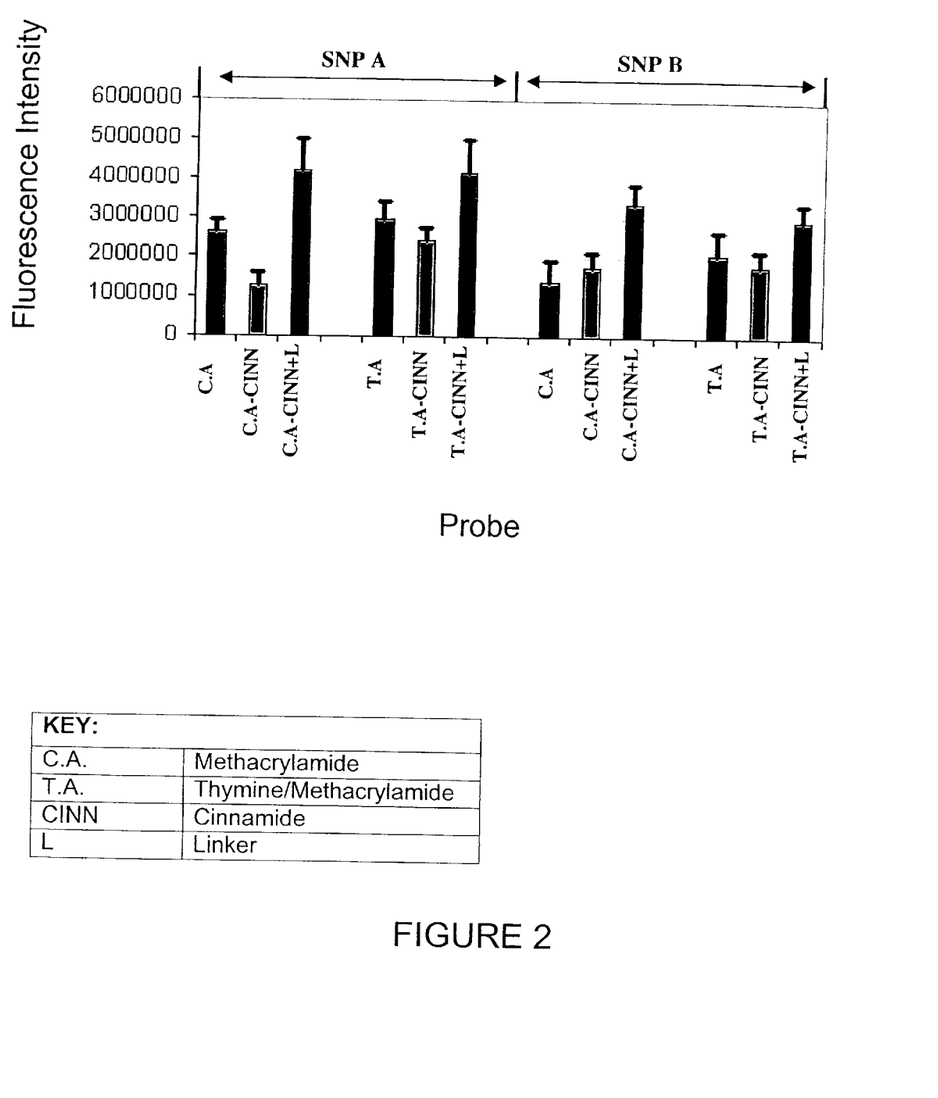
FIG. 2 is a comparison of signaling performance across three attachment chemistries: methacrylamide, cinnamide, and cinnamide with a linker.

In this SNP microarray example, a comparison of signaling performance was done using two different chemistries and length of linker. Specific probes for each allele of a bi-allelic SNP were robotically printed at different locations on the hydrogel. Both probes are required for an individual SNP assay. A fluorescent terminator is incorporated in the event that the correct target is present. The overall performance of the assays conducted on the hydrogel over 12 arrays yielded 15 out of the 16 SNPs calls made at >99% accuracy. Accuracy is defined as the percent correct calls made for every SNP call made as confirmed by sequencing data. Probes attached with cinnamide with a linker yielded higher signal intensities in comparison to either cinnamide alone or methacrylamide attached probes as shown in FIG. 2.

Example 3

This example demonstrates that genes having different expression levels can be measured simultaneously. The cRNA targets for gene expression monitoring on the expression microarray chip are either total RNA or poly(A) mRNA that were amplified and biotin-labeled as described in Lockhart, et al., *Nature Biotechnology*, 14: 1675–80, (1996). In general, poly (A) RNA were converted into double-strand cDNA using T7-d (T)24 oligo primer and SUPERSCRIPT choice system (INVITROGEN, Carlsbad, Calif.). In vitro transcription was performed on those T7 promoter added dsDNA by using T7 transcriptase (MEGA T7 kit, AMBION, Austin, Tex.) for 6 hrs at 37° C. The biotin labeled cRNA was purified by QIAGEN RNEASY column from Qiagen, Inc., Valencia, Calif. and quantitated by measuring absorbance at 260 nm corresponding to 40 μg/mL.

The expression chips were then hybridized using biotin labeled cRNA targets in the concentration of 0.08 μg/μl of buffer containing MOTOROLA HYBRIDIZATION buffer (MOTOROLA LIFE SCIENCES, Northbrook, Ill.) at 37° C. for 18 hrs. The array was then washed with an aqueous buffer containing TRIZMA (SIGMA, St. Louis, Mo.), sodium chloride and TWEEN-20. The chips were then scanned with a Axon Series A scanner.

The gene expression assay was performed using biotin-labeled cRNA generated from human placenta, brain and heart mRNA. Ten 30 mer human gene expression probes which give different expression levels and ten yeast probes were built on the chip. The targets were prepared using human mRNA with different ratios of yeast mRNA added for monitoring the sensitivity and dynamic range of the platform performances. The microarray could detect gene expression at three copy per cell sensitivity.

What is claimed is:

1. A method of performing an expression microarray to determine the presence of a target, comprising:
   (a) attaching a probe which will recognize a target to a polymer-coated support by a [2+2] photocycloaddition to form a microarray;
   (b) contacting an aqueous target solution with the microarray, for a time sufficient to form a complex between complementing targets and probes, wherein the target solution comprises an aqueous buffer solution and the target; and
   (c) scanning the microarray to determine the presence of the target.

2. The method of claim 1, further comprising application of a probe standard to the polymer-coated support.

3. The method of claim 2, wherein the probe and probe standard are applied to the polymer-coated support in about equal amounts, on a weight basis.

4. The method of claim 2, wherein said aqueous target solution further comprises a target standard.

5. The method of claim 1, wherein the concentration of the target is determined through comparison of the fluorescence intensities of the target and target standard.

6. The method of claim 4, wherein the target standard is selected from the group consisting of yeast mRNA and bacterial mRNA, and combinations thereof.

7. The method of claim 1, wherein scanning occurs in a spectrometer capable of measuring and recording fluorescence intensity and position.

8. The method of claim 1, wherein the aqueous target solution comprises a buffer capable of maintaining pH from about 6 to 9.

9. The method of claim 1, wherein the target is a labeled nucleic acid.

10. The method of claim 9, wherein the label is selected from the group consisting of Cy-3, Cy-5, Cy-5.5, and ALEXA FLUOR.

11. The method of claim 9, wherein the label is Cy-3.

12. The method of claim 9, wherein the labeled nucleic acid is mRNA, RNA, DNA, amplified RNA, amplified DNA, and modifications thereof.

13. The method of claim 9, wherein the labeled nucleic acid is mRNA, RNA, or DNA.

14. The method of claim 1, further comprising developing of the microarray after application of the target solution.

15. The method of claim 14, wherein developing lasts from 1 minute to 42 hours.

16. The method of claim 14, wherein developing lasts about 16 hours.

17. The method of claim 14, wherein developing occurs between 30 and 45° C.

18. The method of claim 14, wherein developing occurs at about 37° C.

19. The method of claim 14, further comprising washing with an aqueous wash after developing.

20. The method of claim 19, wherein the aqueous wash contains a buffer capable of maintaining pH from about 6 to 9.

21. The method of claim 20, wherein the buffer comprises phosphate and sodium chloride.

22. The method of claim 1, wherein the solid support is a material selected from the group consisting of nylon, polystyrene, glass, latex, polypropylene, and activated cellulose, and combinations thereof.

23. The method of claim 1, wherein the solid support is glass.

24. The method of claim 1, wherein the polymer is a polymer, reactive prepolymer, or copolymer made of at least two comonomers wherein at least one of said comonomers can undergo [2+2] photocycloaddition.

25. The method of claim 24, wherein the polymer or reactive prepolymer contains polyacrylamide.

26. The method of claim 1, wherein the polymer is a polymer, reactive prepolymer, or copolymer chemically modified to contain a reactive group that undergoes [2+2] photocycloaddition.

27. The method of claim 26, wherein the polymer or reactive prepolymer contains polyacrylamide.

28. The method of claim 1, wherein said probe comprises a nucleic acid fragment containing less than about 1000 nucleotides, and further optionally comprises a linker.

29. The method of claim 28, wherein said linker is an organic chain of about 6 to 100 atoms in length.

30. The method of claim 28, wherein said nucleic acid fragment is selected from the group consisting of synthetic nucleotides and modified nucleotides, and combinations thereof.

31. The method of claim 1, wherein said probe is cDNA.

32. The method of claim 1, wherein said probe is chemically modified to contain a reactive group that undergoes [2+2] photocycloaddition.

33. The method of claim 32, wherein said probe is chemically modified with a phosphoramidite.

34. The method of claim 33, wherein said phosphoramidite is chemically functionalized with a reactive site capable of undergoing [2+2] photocycloaddition.

35. The method of claim 33, wherein said phosphoramidite is functionalized with a cinnamide.

36. The method of claim 1, wherein said probe inherently contains a reactive site that undergoes [2+2] photocycloaddition.

37. The method of claim 34, wherein the reactive site present on the probe(s) contains an alkene group.

38. The method of claim 1, wherein the reactive site present on the polymer and/or the reactive site present on the probe is selected from the group consisting of dimethyl maleimide, maleimide, thymine, polythymine, acrylate, cinnamate, and citraconimide, and combinations thereof.

39. The method of claim 1, wherein the polymer coated support is a hydrogel microarray.

40. The method of claim 39, wherein the microarray is formed by crosslinking a hydrogel simultaneous with step (a).

41. The method of claim 39, wherein prior to step (a) the hydrogel microarray is prepared by first crosslinking a hydrogel.

42. The method of claim 1, wherein a photosensitiser is added during step (a).

43. The method of claim 42 wherein, the photosensitiser is Anthroquinone-2-sulfonic acid.

44. A method of performing a single nucleotide polymorphism microarray to determine the presence of a target, comprising:
(a) attaching a probe which will recognize a target to a polymer-coated support by a [2+2] photocycloaddition to form a microarray;
(b) contacting an aqueous target solution with the microarray, for a time sufficient to form a complex between complementing targets and probes, wherein the target solution comprises an aqueous buffer solution, the target, an active enzyme, and a labeled carrier; and
(c) scanning the microarray to determine the presence of the target.

45. The method of claim 44, further comprising application of a probe standard to the polymer-coated support.

46. The method of claim 45, wherein the probe and probe standard are applied to the polymer-coated support in about equal amounts, on a weight basis.

47. The method of claim 45, wherein said aqueous target solution further comprises a target standard.

48. The method of claim 44, wherein the concentration of the target is determined through comparison of the fluorescence intensities of the target and target standard.

49. The method of claim 47, wherein the target standard is selected from the group consisting of yeast mRNA and bacterial mRNA, and combinations thereof.

50. The method of claim 44, wherein scanning occurs in a spectrometer capable of measuring and recording fluorescence intensity and position.

51. The method of claim 44, wherein the aqueous target solution comprises a buffer capable of maintaining pH from about 6 to 9.

52. The method of claim 44, wherein the aqueous target solution comprises an active enzyme.

53. The method of claim 52, wherein the active enzyme is capable of transferring a label to a probe/target complex by single base extension.

54. The method of claim 52, wherein the active enzyme is thermosequanase.

55. The method of claim 44, wherein the aqueous target solution comprises a fluorescently labeled carrier.

56. The method of claim 55, wherein the fluorescently labeled carrier provides a transferable label to an active enzyme for transfer to a probe/target complex by single base extension.

57. The method of claim 55, wherein the fluorescently labeled carrier is di-deoxynucleotide triphospahte.

58. The method of claim 55, wherein the label is selected from the group consisting of Cy-3, Cy-5, Cy-5.5, and ALEXA FLUOR.

59. The method of claim 55, wherein the label is Cy-3.

60. The method of claim 44, wherein the target is a nucleic acid.

61. The method of claim 60, wherein the nucleic acid is mRNA, RNA, DNA, amplified RNA, amplified DNA, and modifications thereof.

62. The method of claim 60, wherein the nucleic acid is mRNA, RNA, or DNA.

63. The method of claim 44, further comprising developing of the microarray after application of the target solution.

64. The method of claim 63, wherein developing lasts for 30 to 60 heating/cooling cycles.

65. The method of claim 63, wherein developing lasts for 40 to 50 heating/cooling cycles.

66. The method of claim 63, wherein developing occurs between 30 and 70° C.

67. The method of claim 63, wherein developing occurs between 40 and 60° C.

68. The method of claim 63, further comprising washing with an aqueous wash after developing.

69. The method of claim 68, wherein the aqueous wash is performed between 40 and 70° C.

70. The method of claim 68, wherein the aqueous wash is performed between 50 and 60° C.

71. The method of claim 68, wherein the aqueous wash contains a buffer capable of maintaining pH from about 6 to 9.

72. The method of claim 71, wherein the buffer comprises phosphate and sodium chloride.

73. The method of claim 44, wherein the solid support is a material selected from the group consisting of nylon, polystyrene, glass, latex, polypropylene, and activated cellulose, and combinations thereof.

74. The method of claim 44, wherein the solid support is glass.

75. The method of claim 44, wherein the polymer is a polymer, reactive prepolymer, or copolymer made of at least two co-monomers wherein at least one of said co-monomers can undergo [2+2] photocycloaddition.

76. The method of claim 75, wherein the polymer or reactive prepolymer contains polyacrylamide.

77. The method of claim 44, wherein the polymer is a polymer, reactive prepolymer, or copolymer chemically modified to contain a reactive group that undergoes [2+2] photocycloaddition.

78. The method of claim 77, wherein the polymer or reactive prepolymer contains polyacrylamide.

79. The method of claim 44, wherein said probe comprises a nucleic acid fragment containing less than about 1000 nucleotides, and further optionally comprises a linker.

80. The method of claim 79, wherein said linker is an organic chain of about 6 to 100 atoms in length.

81. The method of claim 79, wherein said nucleic acid fragment is selected from the group consisting of synthetic nucleotides and modified nucleotides, and combinations thereof.

82. The method of claim 44, wherein said probe is cDNA.

83. The method of claim 44, wherein said probe is chemically modified to contain a reactive group that undergoes [2+2] photocycloaddition.

84. The method of claim 83, wherein said probe is chemically modified with a phosphoramidite.

85. The method of claim 84, wherein said phosphoramidite is chemically functionalized with a reactive site capable of undergoing [2+2] photocycloaddition.

86. The method of claim 84, wherein said phosphoramidite is functionalized with a cinnamide.

87. The method of claim 44, wherein said probe inherently contains a reactive site that undergoes [2+2] photocycloaddition.

88. The method of claim 83, wherein the reactive site present on the probe(s) contains an electron deficient alkene group.

89. The method of claim 44, wherein the reactive site present on the polymer and/or the reactive site present on the probe is selected from the group consisting of dimethyl maleimide, maleimide, thymine, polythymine, acrylate, cinnamate, and citraconimide, or combinations thereof.

90. The method of claim 44, wherein the polymer coated support is a hydrogel microarray.

91. The method of claim 90, wherein the microarray is formed by crosslinking a hydrogel simultaneous with step (a).

92. The method of claim 90, wherein prior to step (a) the hydrogel microarray is prepared by first crosslinking a hydrogel.

93. The method of claim 44, wherein a photosensitiser is added during step (a).

94. The method of claim 93 wherein, the photosensitiser is Anthroquinone-2-sulfonic acid.

* * * * *